United States Patent [19]

Takiguchi et al.

[11] Patent Number: 5,195,524
[45] Date of Patent: Mar. 23, 1993

[54] FLOW IMAGING METHOD BY MEANS OF AN MRI APPARATUS AND APPARATUS FOR REALIZING SAME

[75] Inventors: Kenji Takiguchi, Kodaira; Etsuji Yamamoto, Akishima; Hideki Kohno, Tama, all of Japan

[73] Assignee: Hitachi, Ltd., Tokyo, Japan

[21] Appl. No.: 647,563

[22] Filed: Jan. 29, 1991

[30] Foreign Application Priority Data

Feb. 2, 1990 [JP] Japan .................................. 2-023973

[51] Int. Cl.⁵ ............................................. A61B 5/055
[52] U.S. Cl. .................... 128/653.3; 324/306; 324/309
[58] Field of Search ............... 128/653.3, 653.2; 324/306, 309

[56] References Cited

U.S. PATENT DOCUMENTS

| | | | |
|---|---|---|---|
| 4,516,582 | 5/1985 | Redington | 128/653.3 |
| 4,520,828 | 6/1985 | Burl et al. | 128/653.3 |
| 4,532,473 | 7/1985 | Wehrli | 128/653.3 |
| 4,602,641 | 7/1986 | Feinberg | 128/653.3 |
| 4,777,957 | 10/1988 | Wehrli et al. | 128/653.3 |
| 4,949,042 | 8/1990 | Kuhara et al. | 128/653.2 |

OTHER PUBLICATIONS

Nishimura et al., "MR Angiography by Selective Inversion Recovery", Magnetic Resonance in Medicine, vol. 4, pp. 193-202, 1987.

*Primary Examiner*—Lee S. Cohen
*Assistant Examiner*—Krista M. Pfaffle
*Attorney, Agent, or Firm*—Antonelli, Terry, Stout & Kraus

[57] ABSTRACT

An MRI flow imaging method and apparatus wherein a width of a relevant region in a direction is set, in which fluid in a subject body flows, and a first 90° radio frequency pulse is applied thereto to excite selectively a relevant region; a gradient magnetic field is applied thereto in a direction, in which it is desired to project the fluid, after an application of a first 90° radio frequency pulse so that a magnetization signal in a projection direction is zero, a second radio frequency pulse is applied to a relevant region to excite the relevant region selectively, after new fluid has poured in the relevant region, an echo signal is measured by applying an encoding gradient magnetic field and a reading out gradient magnetic field in a form of a flow sensitive pulse capable of detecting an echo signal from the fluid, and an echo signal is processed to obtain a two-dimensional image of the fluid.

8 Claims, 5 Drawing Sheets

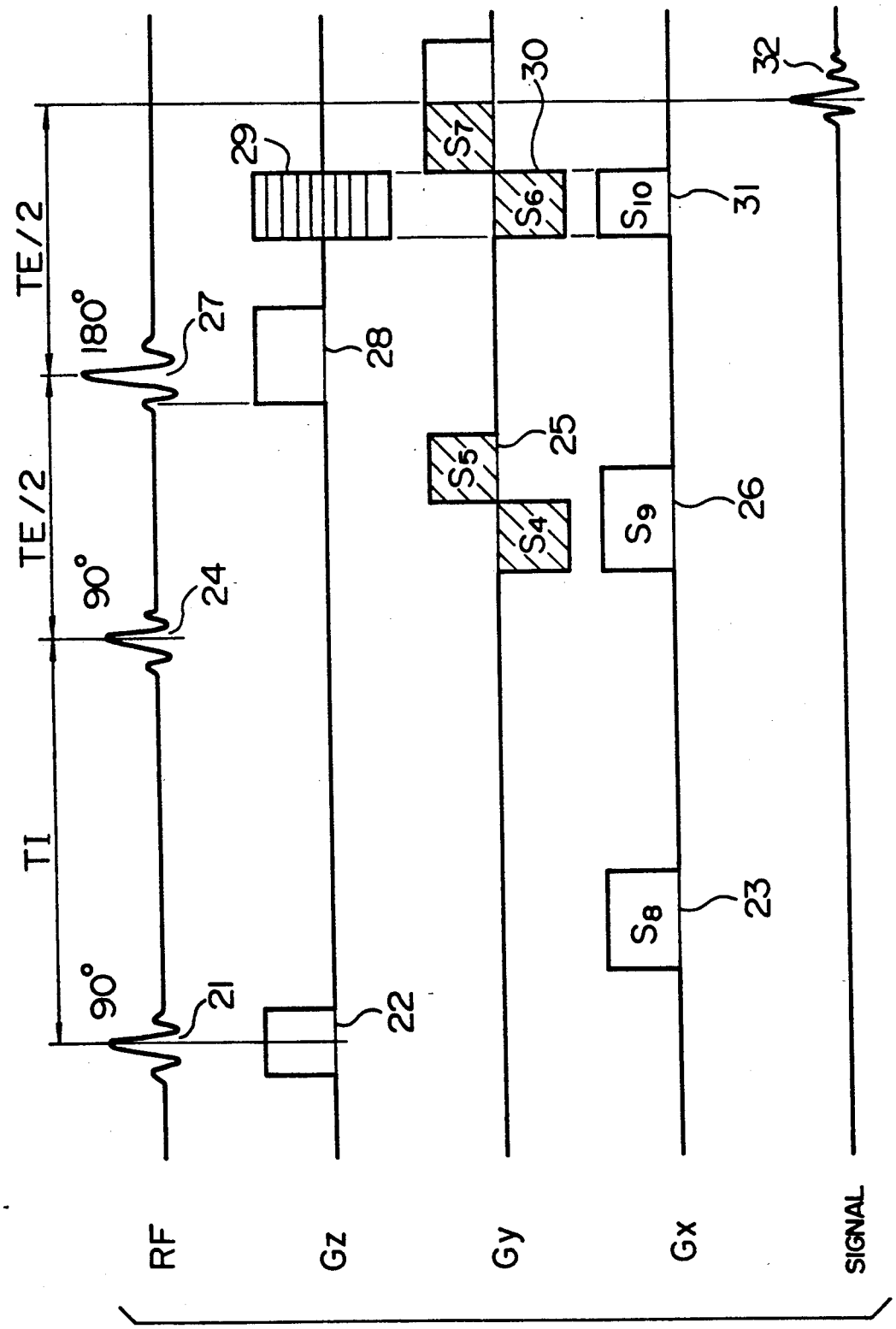

FLOW IMAGING METHOD BY MEANS OF AN MRI APPARATUS AND APPARATUS FOR REALIZING SAME

BACKGROUND OF THE INVENTION

The present invention relates to a flow imaging method by means of an MRI apparatus (hereinbelow called simply flow imaging method and in particular to a flow imaging method and an apparatus for realizing same suitable for blood flow imaging in a human body, etc.

Heretofore, as a blood flow imaging method by means of an MRI apparatus, several methods are generally known, by which an object image is obtained by using a plurality of images having different properties such as represented by an example, by which only the blood flow part is extracted by subtracting one from the other of an image obtained by using a pulse sequence sensitive to a flow and an image obtained by using another pulse sequence, which is not sensitive to the flow.

As one of these method, there is known a method discussed in Magnetic Resonance In Medicine 4, pp. 193-202 (1987). By this method a blood flow image is obtained by using a pulse sequence of radio frequency pulses applied at 180°, 90°, 180° and by subtracting one from the other of images obtained by 2 measurements in the case where the first 180° pulse is used as a selective exciting pulse, by which only the region within the field of view is excited, and the case where it is used as a non-selective exciting pulse, by which a region outside of the field of view is also excited, whereby the component of blood flow excited by the non-selective exciting pulse and pouring in the region within the field of view is imaged.

Further the bolus tracking method is a method, by which, in the spin echo method, the selection plane by the 90° pulse is selected so as to be perpendicular to the blood flow direction and the selection plane by the 180° pulse is selected so as to be parallel to a blood vessel and to include the blood vessel, blood subjected to the 2 exciting pulses being imaged. Although by this method, differing from the subtraction method, it is possible to image blood flow by one measurement, the part, which is imaged, is only a part, where the selection plane by the 90° pulse intersects the selection plane by the 180° pulse, and a part of blood flow, which moves after having been excited by the 90° pulse and is excited again by the 180° pulse. By this method the part of blood blow, which is imaged, is smaller than that imaged by the subtraction method. Consequently this method is used more often in order to measure the flow speed, based on the distance of movement of blood flow and the time interval between the two pulse applications than in order to know the distribution of blood vessel.

Between the prior art techniques described above the subtraction method had a problem that a plurality of images having different properties are necessary and that measurement time for obtaining an object image is long. On the other hand, the bolus tracking method had a problem that although it is unnecessary to effect any subtraction, only blood flow in a restricted region can be observed and it is not possible to observe blood flow sufficient for obtaining blood flow projection.

SUMMARY OF THE INVENTION

The present invention has been done in view of the situations described above and the object thereof is to provide a flow imaging method and an apparatus for realizing same, by means of which it is possible to solve the problems of the prior art techniques described above and to obtain a two-dimensional projection image of blood flow by one measurement.

In order to achieve the above object the flow imaging method according to the present invention comprises the following steps. A gradient magnetic field is applied in the direction where it is desired to project the flow after having selected and excited a relevant region in a region where the fluid flows by applying a 90° radio frequency pulse thereto and magnetization is saturated by disturbing the phase of the excited magnetization. That is, in the relevant region, when magnetization signals are added in the projection direction, they are canceled by each other and the total sum thereof is zero. Next, after new unsaturated flow has poured in the region, the flow, which has newly poured therein, is excited by exciting again the relevant region. Further an encoding gradient magnetic field is applied thereto in the direction perpendicular to the projection direction. Still further a reading out gradient magnetic field is applied thereto in the direction perpendicular both to the projection direction and to the encoding gradient magnetic field to generate an echo signal. A projected image of the flow is obtained by subjecting this signal to image reconstruction.

That is, by the flow imaging method according to the present invention, the magnetization in the relevant region is saturated by the first selective exciting pulse and the gradient magnetic field applied immediately thereafter in the projection direction. Consequently it can be thought that it is only the flow, which pours newly therein and is not saturated, that is excited by the application of the second radio frequency pulse. However, since the magnetization once saturated in the region is restored by longitudinal relaxation between the first applied radio frequency pulse and the second one, the restored component is excited together with the flow, which has newly poured therein. As the result, in the relevant region, a signal of the same kind is produced by a part other than the flow as a spurious signal, although the level thereof is lower than that originated in the fluid part. The gradient magnetic field in the projection direction applied after the second radio frequency pulse disturbs the phase of the excitation signal due to this component restored by longitudinal relaxation to attenuate the spurious signal component and in this way it acts so as to emphasize the echo signal from the normal fluid. Further, in order to obtain a two-dimensional projection image, the encoding gradient magnetic field and the reading out gradient magnetic field are applied in the two directions perpendicular to each other.

In this way it is possible to realize a flow imaging method capable of obtaining a two-dimensional of blood flow by one measurement.

Further, since the selectively excited region is wide and the projection direction is perpendicular to the region selection direction, an effect is obtained that it is possible to obtain a fluid projection image of a wide region, which is different to obtain by the bolus tracking method.

BRIEF DESCRIPTION OF THE DRAWINGS

FIG. 5 is a scheme showing a pulse sequence of another embodiment of the present invention.

DESCRIPTION OF THE PREFERRED EMBODIMENTS

Figure 1:
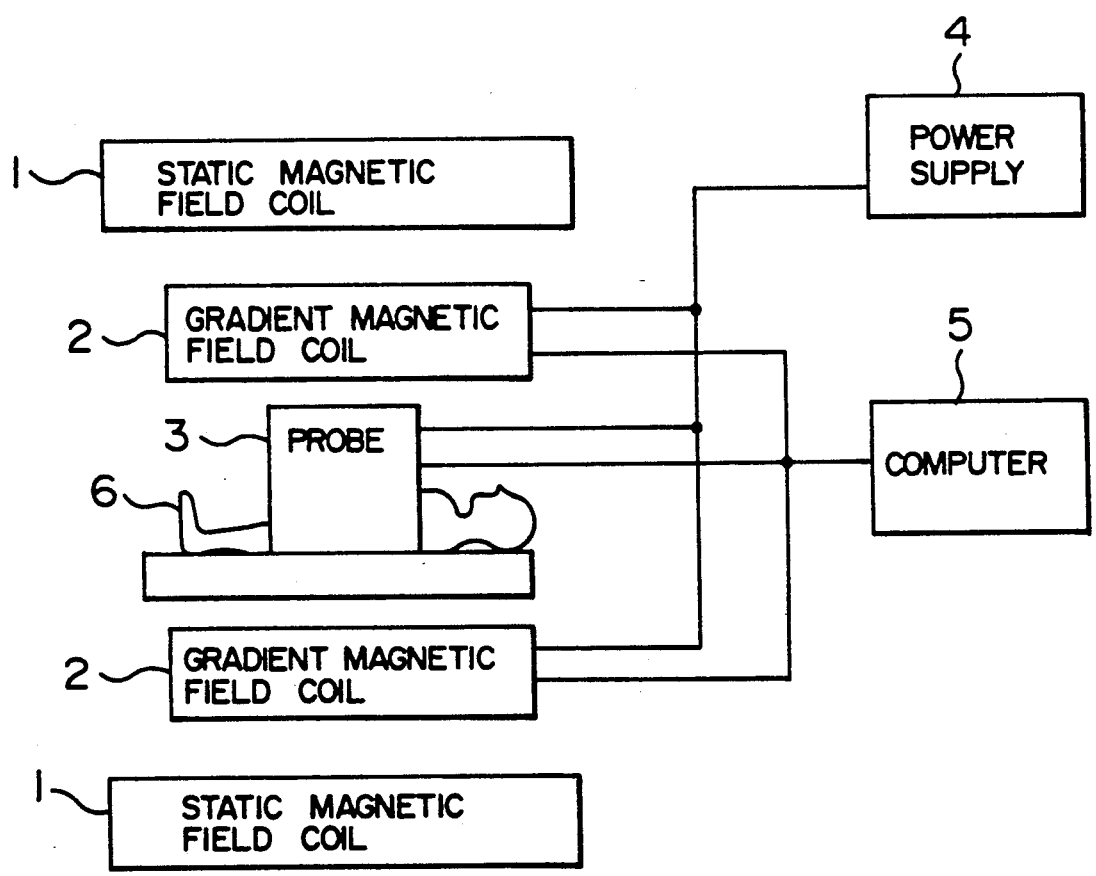
FIG. 1 is a block diagram showing the construction of an MRI apparatus, to which the present invention is applied.

Hereinbelow an embodiment of the present invention will be explained in detail, referring to the drawings.

FIG. 1 shows the outline of the construction of an MRI apparatus, to which the present invention is applied. The present apparatus consists of a coil 1 generating a static magnetic field; a coil 2 generating a gradient magnetic field; a probe 3 transmitting a radio frequency pulse and receiving an echo signal; a power supply 4 for the gradient magnetic field and the radio frequency pulse; and a computer 5. Further 6 represents a subject body.

Figure 2:
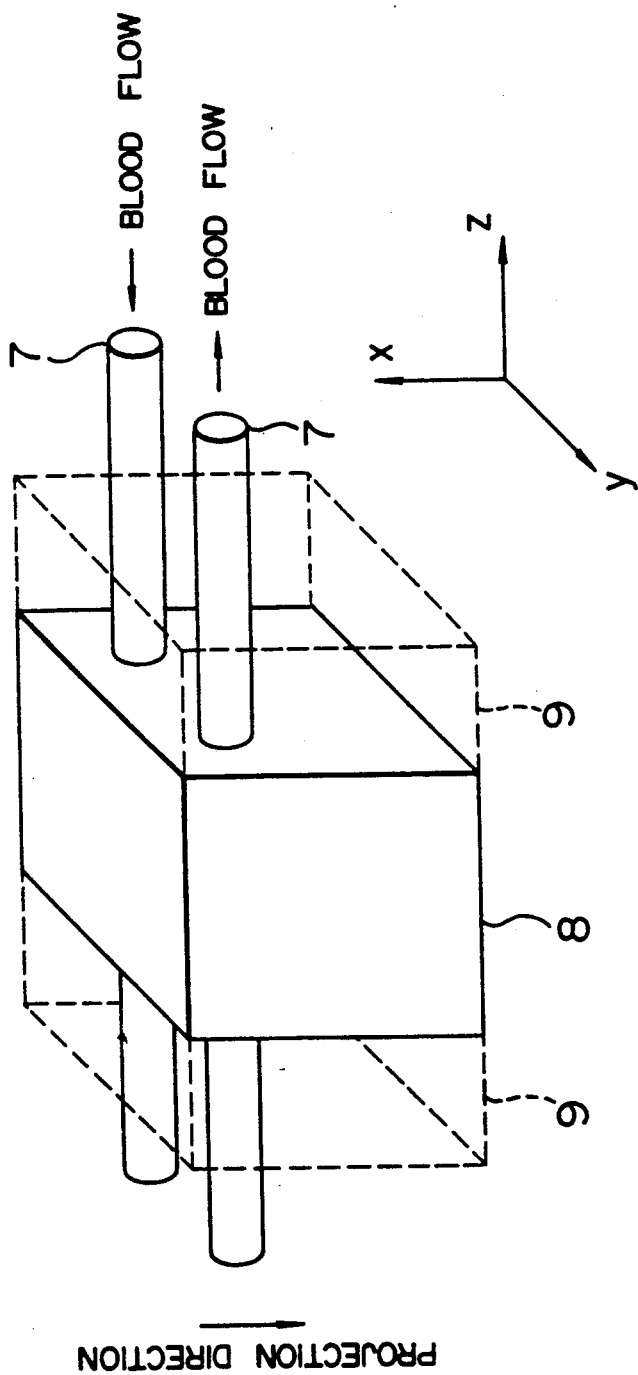
FIG. 2 is a scheme illustrating the relation between the relevant region and the direction of blood flow.

The control of the gradient magnetic field, the radio frequency pulse and taking-in of the signal is effected through the computer 5 according to a pulse sequence. Here, as indicated in FIG. 2, it is supposed that blood flows through a blood vessel 7, traversing a plane perpendicular to the Z-direction, and that a projection image of this blood is obtained. The projection direction is the X-direction. Reference numeral 8 indicates a relevant region and 9 represents regions adjacent thereto.

Figure 3:
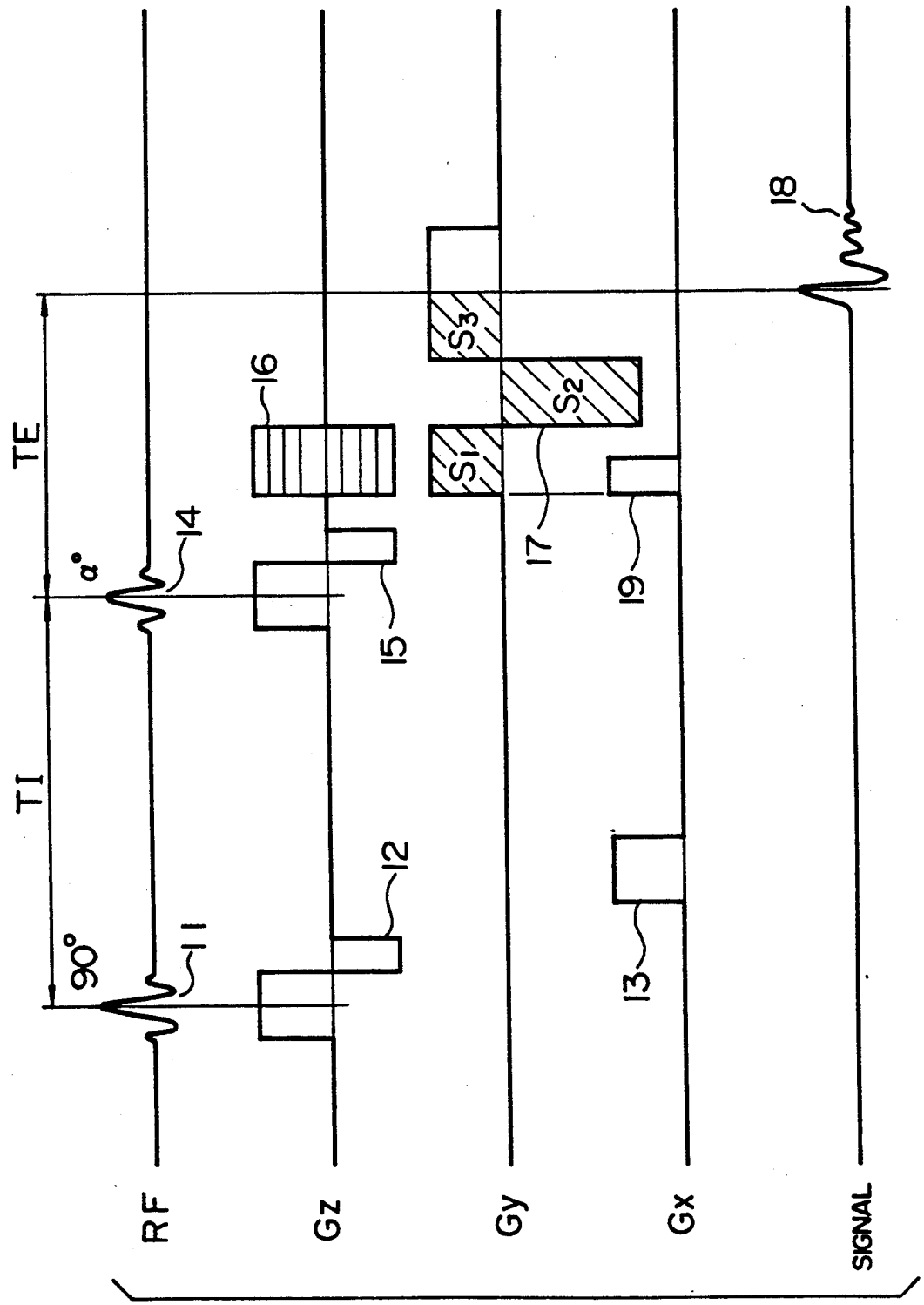
FIG. 3 is a scheme showing a pulse sequence of an embodiment of the present invention.

FIG. 3 shows the pulse sequence in the first embodiment of the present invention. Hereinbelow the operation of the present embodiment will be explained on the basis thereof.

Figure 4A:
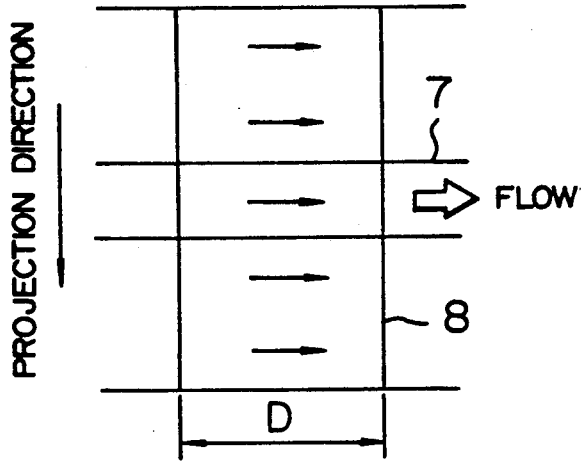
FIGS. 4A to 4E are schemes showing the present invention by using the spin orientation.

At first, the region to be measured is excited by applying thereto a 90° high frequency pulse 11 and a gradient magnetic field ($G_z$) 12, whose magnetic field intensity varies in the Z-direction. The relevant region can be selectively excited by applying the radio frequency pulse and the gradient magnetic field simultaneously thereto. The width of the region selection described above is set so as to be equal to the magnitude of the field of view. The state of spin at this time is shown schematically in FIG. 4A, in which reference numerals indicate the same items in FIG. 2. At first, the total magnetization of the spin in the body takes a direction parallel to the static magnetic field. When the spin is excited, the total magnetization of the spin becomes in the state where it is laid down uniformly by 90° within the width of the relevant region D.

Figure 4D:
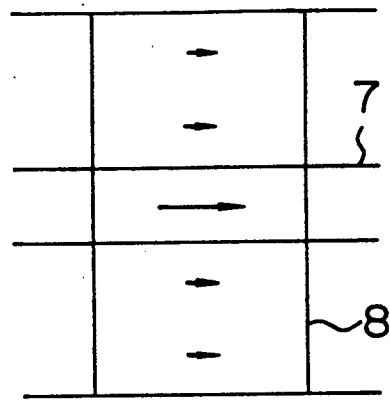
Figure 4B:
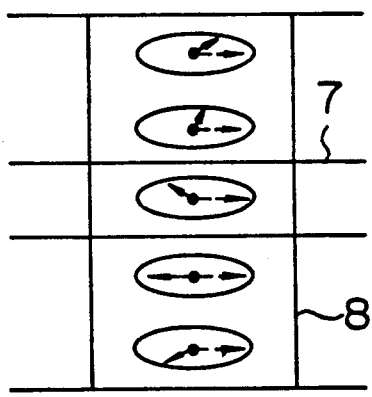
Figure 4E:
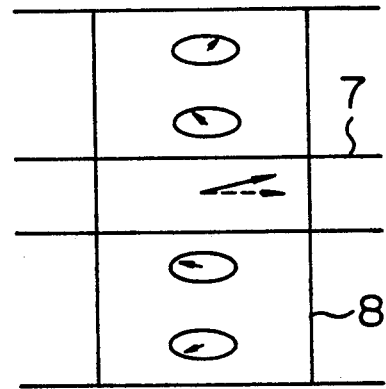
Figure 4C:
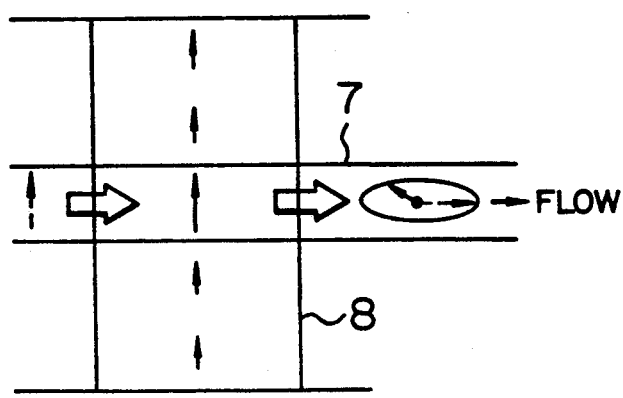

Next a gradient magnetic field ($G_x$) 13, whose magnetic field intensity varies in the X-direction, which is the projection direction, is applied so that the magnetization is saturated by disturbing the phase of the magnetization in the selected region. That is, as indicated in FIG. 4B, the phase is rotated non-uniformly in the horizontal direction by the gradient magnetic field ($G_x$) 13 and magnetization signals in the projection direction are canceled by each other so that the total sum thereof is zero. Then, after TI time therefrom the succeeding radio frequency pulse 14 is applied thereto. During this time, new blood which is not saturated, pours in the region. The spin state at this time is indicated in FIG. 4C. Blood, which is magnetized in a predetermined direction by the static magnetic field, pours in the blood vessel 7 and a signal component due to longitudinal relaxation of the signal excited by a 90° pulse is produced in the relevant region 8 other than the blood vessel. After TI time from the application of the first radio frequency pulse 11, blood, which has poured in the region, is excited by applying a radio frequency pulse 14 and a gradient magnetic field ($G_z$) 15 thereto. The spin state at this time is indicated in FIG. 4D. FIG. 4D shows the case where $\alpha = 90°$. The signal component in the blood vessel is greatest.

An echo signal 18 is received by applying further thereto an encoding gradient magnetic field ($G_z$) 16 in the Z-direction and a reading out gradient magnetic field ($G_y$) 17 in the Y-direction and a blood flow projection image in the X-direction is obtained by subjecting it to a signal processing for the image reconstruction. The reading out gradient magnetic field ($G_y$) 17 applied at this time in the Y-direction is called a flow compensating gradient magnetic field. The role of this flow compensating gradient magnetic field is to compensate the rotation in the phase due to the flow of the blood and it is a gradient magnetic field for obtaining the signal from the blood flow portion, as if the blood remained, similarly to that in the peripheral portion. When the time integral of the gradient magnetic field ($G_y$) 17 is 0 ($S_1 + S_2 + S_3 = 0$), an echo signal 18 is generated.

Further, since the magnetization component within the region, which is restored by the longitudinal relaxation in the time TI, is excited by the application of the second radio frequency pulse 14, it is a signal of the same kind, although the level thereof is lower than that of the signal coming from the blood vessel portion, which gives rise to a spurious signal. The gradient magnetic field ($G_x$) 19 applied in the projection direction (X-direction) after the application of this second radio frequency pulse is applied for attenuating the component of the spurious signal described above in the projection direction. FIG. 4E shows the state of the spin at this time. Similarly to FIG. 4B, the phase of the spurious signal is strongly disturbed and the components in the projection directions are canceled by each other so that the total sum thereof is zero. However, since the level of the signal from the blood vessel portion is high by nature, the rotation in the phase due to the gradient magnetic field ($G_x$) 19 is small.

At this time, influences of this gradient magnetic field on the blood in a blood vessel, which is fine with respect to the thickness of the relevant region in the projection direction are small and therefore it is possible to extract only the signal from the blood. Inversely speaking, it is necessary that the thickness of the relevant region is sufficiently greater than the magnitude of the object blood vessel for which the blood flow imaging is effected.

As a second embodiment, FIG. 5 shows a pulse sequence by the spin echo method for obtaining an echo signal by exciting blood flow, which has poured in the saturated region and thereafter refocusing it by means of an inverted pulse. Similarly to the first embodiment described previously, it is supposed that the blood traverses a plane perpendicular to the Z-direction, as indicated in FIG. 2, to obtain a projection image of this blood, the projection direction being the X-direction.

At first, a 90° radio frequency pulse 21 and the gradient magnetic field ($G_z$) 22 in the Z-direction are applied to the region, which is to be measured, to excite it. The width of the selected region is so set that it is equal to the extent of the fluid of view.

Next the gradient magnetic field ($G_x$) 23 is applied thereto in the X-direction, which is the projection direction and the magnetization is saturated by disturbing the phase of magnetization in the selected region. Thereafter, after a time TI the succeeding radio frequency pulse 24 is applied. During this period of time new blood, which is not saturated, pours in the region.

After the time TI from the application of the first radio frequency pulse 21, a 90° radio frequency pulse 24 of non-selective excitation is applied so that the blood, which has poured in a region outside of the relevant region and in the relevant region, is excited to lay down the spin by 90°. Since the direction of the spin for the blood, which pours further in the region before the succeeding 180° radio frequency pulse 27 is applied, is identical to the direction of the spin in the blood selectively excited in the region, it is possible to refocus it by using the 180° radio frequency pulse 27 without dealing with the lapse of time. The 180° radio frequency pulse 27 and the gradient magnetic field ($G_z$) 28 in the Z-direction are applied after a time TE/2 from the application of the 90° radio frequency pulse 24. In this way it is possible to refocus the magnetization in the region.

The echo signal 32 is received by applying further the encoding gradient magnetic field ($G_z$) 29 in the Z-direction and the reading out gradient magnetic field ($G_y$) 30. A blood flow projection image in the X-direction is obtained by subjecting the signal to an image reconstructing signal processing. Further, at this time, the reading out gradient magnetic fields ($G_y$) 25 and 30 in the Y-direction before and after the 180° radio frequency pulse 27 are flow compensate gradient magnetic fields similarly to the gradient magnetic field ($G_y$) 17 indicated in FIG. 2. In the present embodiment, in order to shorten the time after the application of the 90° pulse until the signal 32 is obtained, it is divided into two parts. When the time integral value is zero ($S_4+S_5+S_6+S_7=0$), the signal 32 is obtained.

Still further, the gradient magnetic fields ($G_x$) 26 and 31 in the X-direction applied before and after the 180° radio frequency pulse 27 are applied, similarly to the gradient magnetic fields ($G_x$) 13 and 19 indicated in FIG. 2, for attenuating spurious signals generated by the magnetization restored by the longitudinal relaxation in the time TI and spurious signals generated by non-uniformity in the static magnetic field and the radio frequency pulses. However, in the case where the time integral values of the gradient magnetic fields in the X-direction before and after the 180° radio frequency pulse 27 are equal to each other, since this is equivalent to the case where no gradient magnetic field in the X-direction is applied, it has no effect with respect to the latter spurious signals. Therefore, here, the time integral values of the gradient magnetic fields described above before and after the 180° radio frequency pulse 27 are set so as not to be equal to each other. That is, they are set so that $S_8+S_9-S_{10}=0$.

The embodiments described above indicate only examples of the present invention is not restricted thereto. For example, the present invention can be applied not only to the blood flow imaging in a human body, but also to other flow imagings.

We claim:

1. A flow imaging method utilizing an MRI apparatus comprising the steps of:

(a) setting a width of a relevant region in a flow direction, in which fluid in a subject body flows, and applying a first 90° radio frequency pulse thereto to excite selectively said relevant region;
   (b) applying a gradient magnetic field thereto in a projection direction, in which it is desired to project said fluid, whereby a phase of magnetization excited by said first 90° radio frequency pulse in said relevant region is disturbed to saturate magnetization;
   (c) waiting a predetermined time until new fluid pours in said relevant region;
   (d) applying a second radio frequency pulse to said relevant region after a lapse of said predetermined time to excite said relevant region selectively;
   (e) applying said gradient magnetic field in said projection direction;
   (f) applying an encoding gradient magnetic field in a direction perpendicular to said projection direction and further applying a reading out gradient magnetic field in a direction perpendicular both to said projection direction and to said encoding gradient magnetic field in a form of a flow compensating pulse so as to detect an echo signal from said fluid;
   (g) measuring said echo signal from said subject body; and
   (h) processing said echo signal to obtain a two-dimensional image of said fluid.

2. A flow imaging method according to claim 1, wherein a thickness of said relevant region is chosen so as to be sufficiently greater than a size of a vessel through which said fluid flows.

3. A flow imaging method utilizing an MRI apparatus comprising the steps of:

(a) setting a width of a relevant region in a flow direction, in which fluid in a subject body flows, and applying a first 90° radio frequency pulse thereto to excite selectively said relevant region;
   (b) applying a gradient magnetic field thereto in a projection direction, in which it is desired to project said fluid, whereby a phase of magnetization excited by said first 90° radio frequency pulse in said relevant region is disturbed to saturate magnetization;
   (c) waiting a first predetermined time until new fluid pours in said relevant region;
   (d) applying a second 90° radio frequency pulse to said relevant region after a lapse of said first predetermined time to excite said subject body non-selectively;
   (e) applying said gradient magnetic field in said projection direction;
   (f) applying a 180° radio frequency pulse to said relevant region after a second predetermined time has lapsed from an application of said second radio frequency pulse to excite selectively said relevant region;
   (g) applying said gradient magnetic field in said projection direction;
   (h) applying an encoding gradient magnetic field in a direction perpendicular to said projection direction and further applying a reading out gradient magnetic field in a direction perpendicular both to said projection direction and to said encoding gradient magnetic field, said read out gradient magnetic field being applied so as to detect an echo signal from said fluid;

(i) measuring said echo signal from said subject body; and (j) processing said echo signal to obtain a two-dimensional image of said fluid.

4. A flow imaging method according to claim 3, wherein an application time and an intensity of said gradient magnetic field applied before and after said 180° radio frequency pulse in the projection direction are so chosen that time integral values of said gradient magnetic fields are not equal.

5. A flow imaging method according to claim 3, wherein a thickness of said relevant region is chosen so as to be sufficiently greater than a size of a vessel through which said fluid flows.

6. An MRI imaging apparatus comprising:
(a) static magnetic field generating means;
(b) means for generating gradient magnetic fields independently in three perpendicular directions;
(c) means for applying a first 90° radio frequency pulse to a subject body to excite the subject body selectively so that a flow direction, in which fluid flows in said subject body, is in a width direction of a relevant region;
(d) means for applying said gradient magnetic field thereto in a projection direction, in which it is desired to project said fluid, after an application of said first 90° radio frequency pulse, whereby a phase of magnetization excited by said first 90° radio frequency pulse in said relevant region is disturbed to saturate magnetization;
(e) means for applying a second radio frequency pulse to said relevant region to excite said relevant region selectively, when new fluid pours in said relevant region, after a predetermined time has lapsed from an application of said first 90° radio frequency pulse;
(f) means for applying said gradient magnetic field in said projection direction after an application of said second radio frequency pulse;
(g) means for applying an encoding gradient magnetic field in a direction perpendicular to said projection direction;
(h) means for applying a reading out gradient magnetic field in a direction perpendicular both to said projection direction and to said encoding gradient magnetic field in a form of a flow compensating pulse so as to detect an echo signal from said fluid;
(i) means for measuring said echo signal from said subject body; and
(j) means for processing said echo signal to obtain a two-dimensional image of said fluid.

7. An MRI flow imaging apparatus comprising:

(a) static magnetic field generating means;
(b) means for generating gradient magnetic fields independently in three perpendicular directions;
(c) means for applying a first 90° radio frequency pulse to a subject body to excite said subject body selectively so that a flow direction, in which fluid flows in said subject body, is in a width direction of a relevant region;
(d) means for applying said gradient magnetic field thereto in a projection direction, in which it is desired to project said fluid, after an application of said first 90° radio frequency pulse, whereby a phase of magnetization excited by said first 90° radio frequency pulse in said relevant region is disturbed to saturate magnetization;
(e) means for applying a second radio frequency pulse to said relevant region to excite said relevant region non-selectively, when new fluid pours in said relevant region, after a first predetermined time has lapsed from an application of said first 90° radio frequency pulse;
(f) means for applying said gradient magnetic field in said projection direction after an application of said second 90° radio frequency pulse;
(g) means for applying a 180° radio frequency pulse to said relevant region to excite said relevant region selectively, when a second predetermined time has lapsed after an application of said second radio frequency pulse;
(h) means for applying said gradient magnetic field in said projection direction after an application of said 180° radio frequency pulse;
(i) means for applying an encoding gradient magnetic field in a direction perpendicular to said projection direction;
(j) means for applying a reading out gradient magnetic field in a direction perpendicular both to said projection direction and to said encoding gradient magnetic field in a form of a flow compensating pulse so as to detect an echo signal from said fluid;
(k) means for measuring said echo signal from said subject body; and
(l) means for processing said echo signal to obtain a two-dimensional image of said fluid.

8. An MRI flow imaging apparatus according to claim 7, wherein said means for applying said gradient magnetic field in said projection direction before and after an application of said 180° radio frequency pulse includes means for selecting an application time and an intensity of said gradient magnetic field such time integral values of said gradient magnetic fields are not equal.

* * * * *